United States Patent [19]

Cross et al.

[11] Patent Number: 4,835,165
[45] Date of Patent: May 30, 1989

[54] ANTIARRHYTHMIC 4-PHENYLPIPERIDINES

[75] Inventors: Peter E. Cross, Canterbury; Roger P. Dickinson, Dover, both of England

[73] Assignee: Pfizer Inc., New York, N.Y.

[21] Appl. No.: 175,071

[22] Filed: Mar. 30, 1988

[30] Foreign Application Priority Data

May 2, 1987 [GB] United Kingdom ............... 8710494

[51] Int. Cl.$^4$ .................. A61K 31/445; C07D 401/04
[52] U.S. Cl. .................................... 514/318; 514/326;
546/194; 546/210
[58] Field of Search ............... 546/194, 210; 514/318,
514/326

[56] References Cited

U.S. PATENT DOCUMENTS 4,263,438  4/1981  Althuis et al. .................. 546/194

FOREIGN PATENT DOCUMENTS 0021973  1/1981  European Pat. Off. .
0045980  2/1982  European Pat. Off. .
0235752  9/1987  European Pat. Off. .
3730M   12/1965  France .

OTHER PUBLICATIONS

*Chemical Abstracts*, 67:100103M (1967) [Jain, P., et al., *J. Med. Chem.* 10(5), 812–818 (1967)].

Primary Examiner—Richard A. Schwartz
Attorney, Agent, or Firm—Peter C. Richardson; Lawrence C. Akers; Paul H. Ginsburg

[57] ABSTRACT

A cardiac antiarrhythmic agent of the formula:

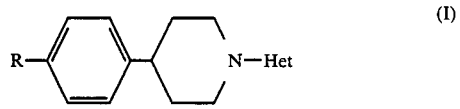

or a pharmaceutically acceptable salt thereof; wherein
R is $R^3SO_2NH-$, $R^3CONH-$ or $R^1R^2NSO_2-$;
$R^1$ and $R^2$ are each independently H or $C_1$–$C_4$ alkyl;
$R^3$ is $C_1$–$C_4$ alkyl, $C_3$–$C_7$ cycloalkyl or $-NR^1R^2$ where $R^1$ and $R^2$ are as defined above; and
Het is either (a) a 2-, 3- or 4-pyridyl group optionally substituted by a $C_1$–$C_4$ alkyl or an amino group, or (b) a 2-imidazolyl group optionally substituted by one or two $C_1$–$C_4$ alkyl groups.

10 Claims, No Drawings

ANTIARRHYTHMIC 4-PHENYLPIPERIDINES

This invention relates to certain phenylpiperidine derivatives which are antiarrhythmic agents useful in the treatment of cardiac arrhythmias.

The compounds of the invention prolong the duration of the action potential in cardiac muscle and conducting tissue, and thereby increase refractoriness to premature stimuli. Thus, they are Class III anti-arrhythmic agents according to the classification of Vaughan Williams (Anti-Arrhythmic Action, E. M. Vaughan Williams, Academic Press, 1980). They are effective in atria, ventricles and conducting tissue both in vitro and in vivo and are therefore useful for the prevention and treatment of a wide variety of ventricular and supraventricular arrhythmias including atrial and ventricular fibrillation. Because they do not alter the speed at which impulses are conducted, they have less propensity than current drugs (mostly Class I) to precipitate or aggravate arrhythmias, and they also produce less neurological side effects. Some of the compounds also have positive inotropic activity and therefore are particularly beneficial in patients with impaired cardiac pump function.

Thus the invention provides phenyl-piperidine derivatives of the formula:

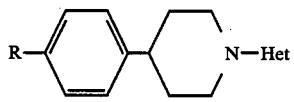

(I)

and their pharmaceutically acceptable salts, wherein
R is $R^3SO_2NH-$, $R^3CONH-$ or $R^1R^2NSO_2-$;
$R^1$ and $R^2$ are each independently H or $C_1$–$C_4$ alkyl;
$R^3$ is $C_1$–$C_4$ alkyl, $C_3$–$C_7$ cycloalkyl or $-NR^1R^2$ where $R^1$ and $R^2$ are as defined above; and
Het is either (a) a 2-, 3- or 4-pyridyl group optionally substituted by a $C_1$–$C_4$ alkyl or an amino group, or (b) a 2-imidazolyl group optionally substituted by one or two $C_1$–$C_4$ alkyl groups.

The preferred alkyl group is methyl.

The pharmaceutically acceptable salts of the compounds of the formula (I) include acid addition salts formed from acids which form non-toxic salts such as the hydrochloride, hydrobromide, hydroiodide, sulphate or bisulphate, phosphate or hydrogen phosphate, acetate, maleate, fumarate, lactate, tartrate, citrate, gluconate, benzoate, methanesulphonate, benzenesulphonate and p-toluenesulphonate salts. Some of the compounds, e.g. those in which R is $R^3SO_2NH-$, may also form metal salts, particularly alkaline earth and alkali metal salts. Examples include the sodium and potassium salts.

The invention also includes any novel intermediates disclosed herein, such as those of the formulae (II), (IV), (V) and (VIII).

Particularly important intermediates are those of the formula:

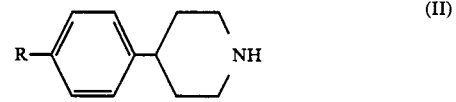

(II)

where R is as defined for formula (I), and:

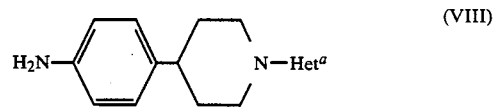

(VIII)

where $Het^a$ is a group as defined for Het in formula (I) except for amino-pyridyl.

The compounds of the formula (I) can be prepared by the following routes:

(1) The compounds of the formula (I) wherein "Het" is pyridyl or $C_1$–$C_4$ alkyl-substituted pyridyl can be prepared by reacting a 4-phenyl-piperidine (II) with a halo-pyridine (III) according to the following reaction scheme:

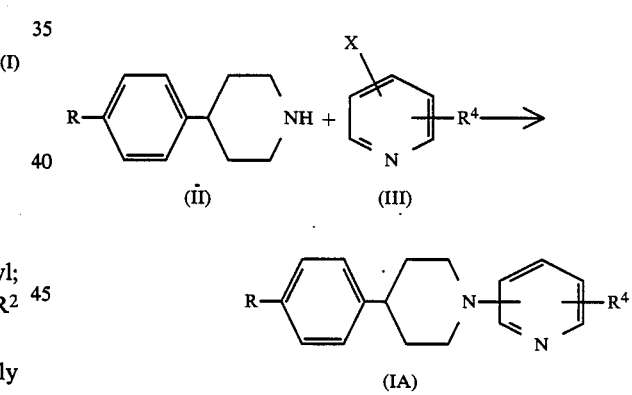

where R is as defined for formula (I), X is halo (preferably chloro or bromo) and $R^4$ is H or $C_1$–$C_4$ alkyl. The reaction is typically achieved by heating the reactants, e.g. at 60°–130° C. and preferably under reflux, in approximately equimolar proportions in a reaction-inert organic solvent, e.g. n-butanol or isoamyl alcohol, and preferably in the presence of an acid acceptor such as sodium bicarbonate. It is in fact preferable to use the compound (III) in acid addition salt form in the presence of, e.g., sodium bicarbonate.

The product (IA) can then be isolated and purified conventionally.

The starting materials of the formula (II) can for example be prepared by the following methods:

(a)

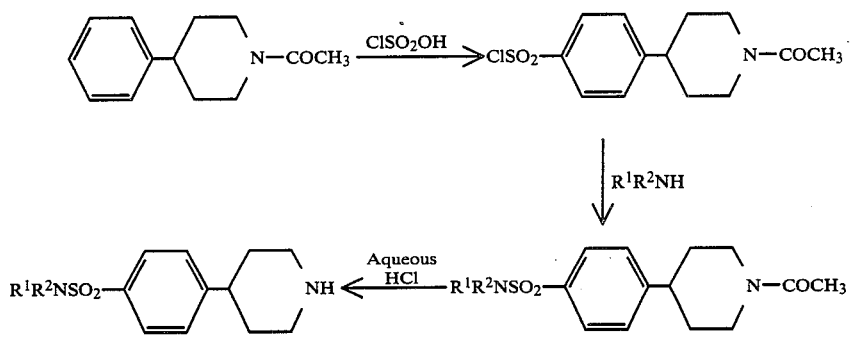

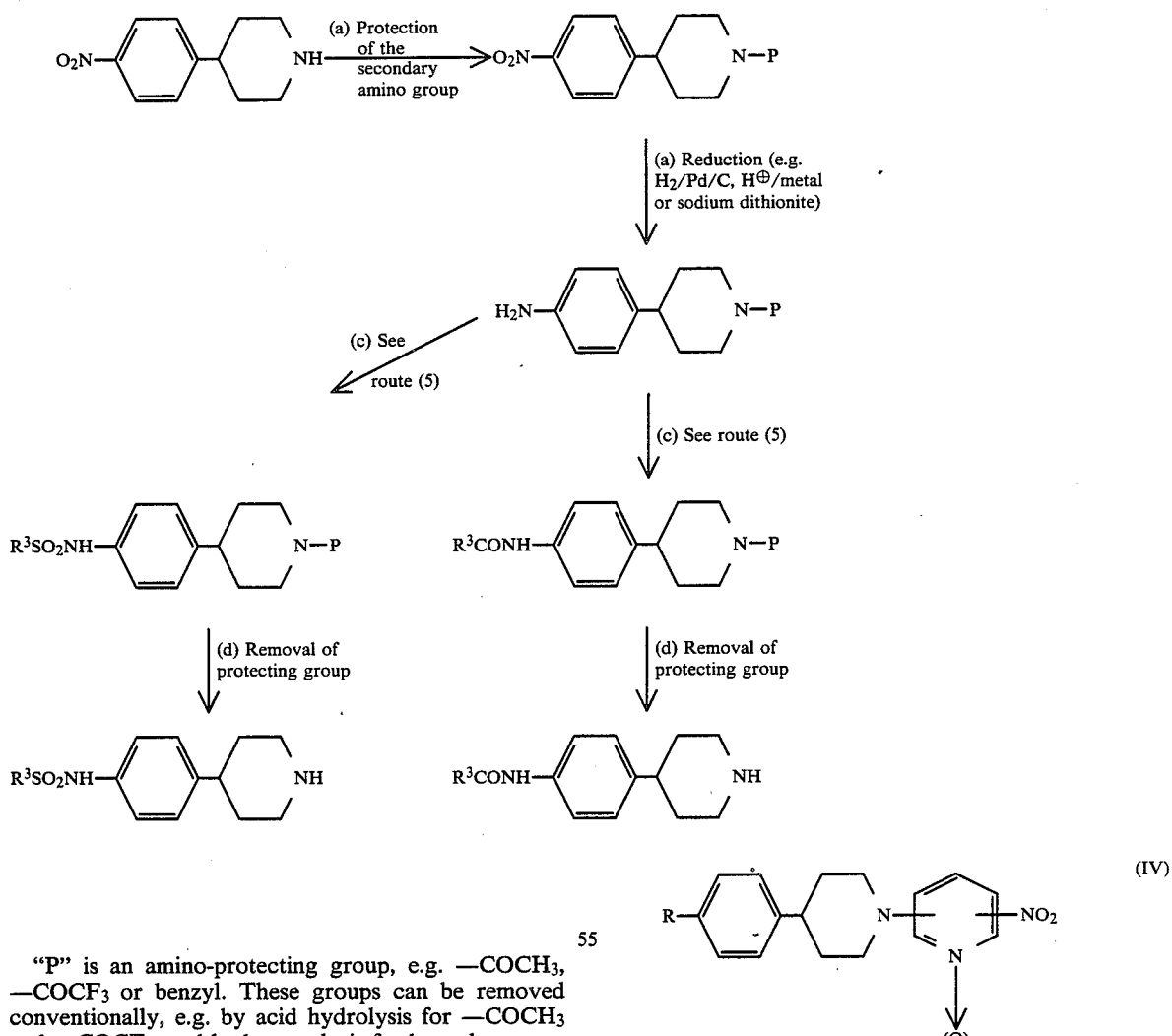

"P" is an amino-protecting group, e.g. —COCH₃, —COCF₃ or benzyl. These groups can be removed conventionally, e.g. by acid hydrolysis for —COCH₃ and —COCF₃, and hydrogenolysis for benzyl.

$R^3$ is as defined for formula (I). The reactions of step (c) can be carried out as described in route (5) which follows.

The starting materials of the formula (III) are known compounds.

(2) In the case where "Het" is amino-substituted pyridyl, the desired compounds of the formula (I) are best prepared by the reduction of a compound of the formula:

wherein R is as defined for formula (I) and n is 0 or 1.

The reduction of the nitro group and, if present, the N-oxide, is achieved by conventional methods, for example by catalytic hydrogenation, e.g. over a palladium on charcoal catalyst in a suitable organic solvent, e.g. ethanol/acetic acid.

The nitro-containing intermediates of the formula (IV) can be prepared by the method of route (1) above starting with the appropriate halo-substituted nitro-pyridine or nitro-pyridine-N-oxide.

(3) The compounds of the formula (I) in which "Het" is amino-substituted pyridyl can also be prepared by hydrolysing a compound of the formula:

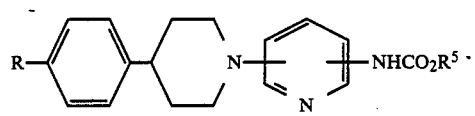

(V)

wherein $R^5$ is $C_1$–$C_4$ alkyl and R is as defined for formula (I).

The reaction is readily achieved by acid or base hydrolysis in an aqueous solvent. For example the reaction can be carried out by heating the compound of formula (V) in aqueous sodium hydroxide under reflux for several hours. The solution is then neutralised and extracted with an organic solvent to recover the desired product of the formula (I).

The starting materials of the formula (V) are preparable as follows:

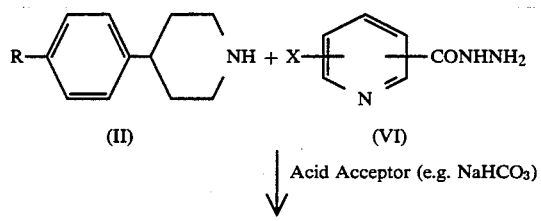

Acid Acceptor (e.g. NaHCO₃)

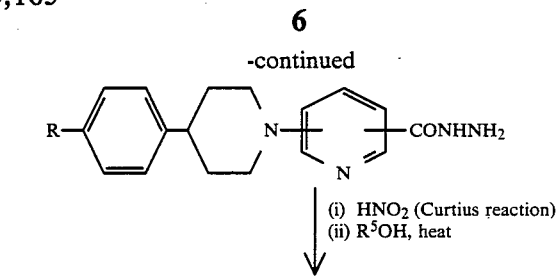

(i) HNO₂ (Curtius reaction)
(ii) R⁵OH, heat

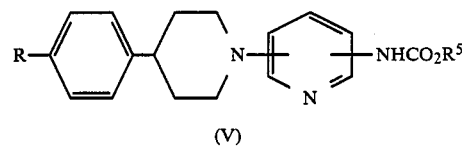

(V)

X is halo, $R^5$ is $C_1$–$C_4$ alkyl and R is as defined for formula (I).

(4) The compounds of the formula (I) wherein "Het" is imidazolyl or $C_1$–$C_4$ alkyl-substituted imidazolyl are preparable from a 4-substituted-phenyl-piperidine of the formula (II) as shown in the following reaction scheme wherein $R^6$ is H or $C_1$–$C_4$ alkyl, $R^7$ is $C_1$–$C_4$ alkyl, $R^8$ and $R^9$ are each independently H or $C_1$–$C_4$ alkyl, each $R^{10}$ is $C_1$–$C_4$ alkyl or the two groups $R^{10}$ are joined to form a $C_2$–$C_3$ alkylene chain, and Q is halo—preferably iodo; with the proviso that not more than two of $R^6$, $R^8$ and $R^9$ in formula (IB) are $C_1$–$C_4$ alkyl.

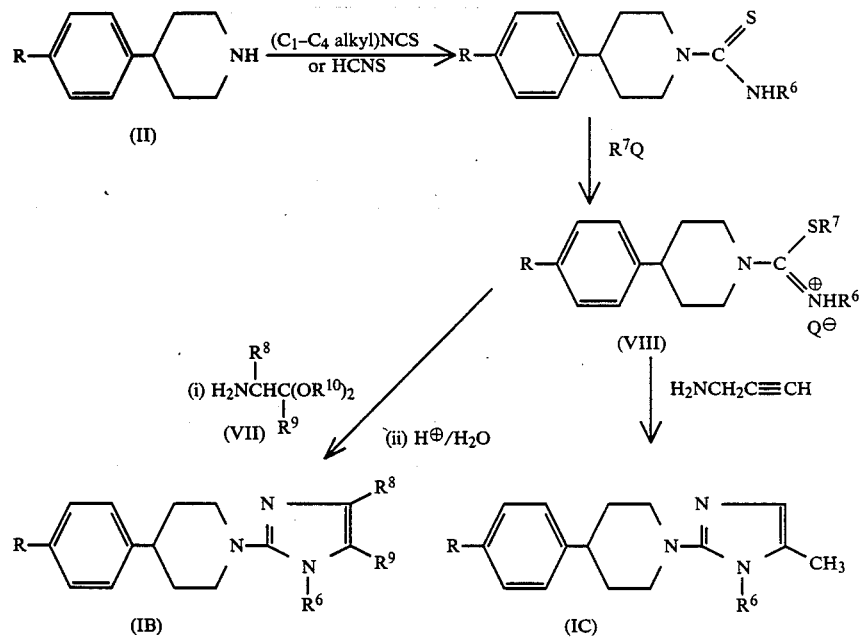

In the first step, the phenyl-piperidine (II) is either (a) reacted with a $C_1$–$C_4$ alkyl isothiocyanate in a suitable organic solvent, e.g. methanol or dichloromethane, at about room temperature to give a carbothioamide in which $R^6$ is $C_1$–$C_4$ alkyl, or (b) reacted with a thiocyanate salt, e.g. ammonium, sodium or potassium thiocyanate under acidic conditions, to give a carbothioamide in which R is H.

The carbothioamide is then S-alkylated using a $C_1$–$C_4$ alkyl halide (e.g. an iodide) or dialkyl sulphate.

The S-alkyl derivative can then be cyclised by two different methods.

In the first method, the S-alkyl derivative is reacted with the acetal (VII), e.g. by heating at from 60°-130° C. and preferably under reflux in a suitable organic solvent, such as pyridine, to form an intermediate guanidine. The guanidine is then heated in aqueous acid, e.g. aqueous hydrochloric acid, and preferably under reflux, to cyclise it to the product (IB).

In the second method, the S-alkyl derivative is cyclised to the product (IC) by reaction with propargylamine in a suitable organic solvent, e.g. pyridine, and typically at a temperature of from 60°-130° C. and preferably under reflux.

(5) The compounds of the formula (I) in which R is $R^3SO_2NH-$ or $R^3CONH-$ where $R^3$ is as defined for formula (I) and Het is as defined for formula (I) other than amino-pyridyl can also be prepared from a compound of the formula:

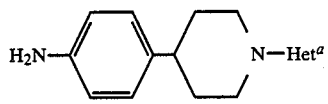
(IX)

where $Het^a$ is a group as defined for Het in formula (I) except for amino-pyridyl, by one of the following routes:

(a) Reaction with a sulphonyl chloride or bromide of the formula $R^{11}SO_2Cl$ or $R^{11}SO_2Br$ or sulphonic anhydride of the formula $(R^{11}SO_2)_2O$ where $R^{11}$ is $C_1$-$C_4$ alkyl or $C_3$-$C_7$ cycloalkyl to give a compound of the formula (I) in which R is $(C_1$-$C_4$ alkyl$)SO_2NH-$ or $(C_3$-$C_7$ cycloalkyl$)SO_2NH-$.

The reaction is typically carried out in a suitable organic solvent at room temperature, and optionally in the presence of a base ("acid acceptor") such as pyridine, triethylamine, sodium bicarbonate or potassium carbonate. The presence of an acid acceptor is especially useful when a sulphonyl chloride or bromide is used as the acylating agent. It is preferred to use either the sulphonic anhydride $(R^{11}SO_2)_2O$ in methylene chloride or sulphonyl chloride $R^{11}SO_2Cl$ in pyridine for the sulphonylation. The product can then be isolated and purified by conventional techniques.

(b) Reaction with a sulphamoyl chloride of the formula $R^1R^2NSO_2Cl$ where $R^1$ and $R^2$ are as defined for formula (I) except that at least one of $R^1$ and $R^2$ is a $C_1$-$C_4$ alkyl group to give a compound of the formula (I) in which R is $R^1R^2NSO_2NH-$ where $R^1$ and $R^2$ are as defined in this method;

(c) Reaction with sulphamide, e.g. by refluxing in dioxan, to give a compound of the formula (I) in which R is $H_2NSO_2NH-$;

(d) Reaction with an acyl halide of the formula $R^{11}COCl$ or $R^{11}COBr$ or anhydride of the formula $(R^{11}CO)_2O$ where $R^{11}$ is as defined in (a) to give a compound of the formula (I) in which R is $(C_1$-$C_4$ alkyl$)CONH-$ or $(C_3$-$C_7$ cycloalkyl$)CONH-$;

(e) Reaction with a $C_1$-$C_4$ alkyl isocyanate, e.g. in an organic solvent such as dimethylformamide at about room temperature, to give a compound of the formula (I) in which R is $(C_1$-$C_4$ alkyl$)NHCONH-$;

(f) Reaction with an alkali metal cyanate (preferably sodium or potassium cyanate) under aqueous acidic conditions to give a compound of the formula (I) in which R is $H_2NCONH-$; and (g) Reaction with a compound of the formula $(C_1$-$C_4$ alkyl$)_2NCOCl$ to give a compound of the formula (I) in which R is $(C_1$-$C_4$ alkyl$)_2NCONH-$.

The starting materials of the formula (VIII) can be prepared according to the method of routes (1) and (4) using a 4-(4-nitrophenyl)piperidine in place of the compound (II) followed by reduction of the nitro group to amino by a conventional method, e.g. by using $H_2/Pd/C$.

All of the above reactions are conventional and appropriate reagents and reaction conditions for their performance and procedures for isolating the desired products will be well known to those skilled in the art in accordance with literature precedents and by reference to the Examples hereto.

Pharmaceutically acceptable salts are readily prepared by mixing solutions containing equimolar amounts of the free base and the desired acid. The salt generally precipitates from solution or is recovered by evaporation of the solvent.

The biological activity of the compounds of the invention is assessed by measuring the effect of the compounds on atrial refractoriness. In this test guinea pig right hemiatria are mounted in a bath containing physiological salt solution, with one end connected to a force transducer. The tissues are stimulated at 1 Hz using field electrodes. Effective refractory period (ERP) is measured by introducing premature stimuli ($S_2$) after every 8th basic stimulus ($S_1$). The $S_1S_2$ coupling interval is gradually increased until $S_2$ reproducbily elicits a progagated response. This is defined as the ERP. The test compound is then added to the bath and the concentration of compound required to increase ERP by 25% is determined ($ED_{25}$). ERP is also measured in guinea pig right papillary muscles incubated in physiological saline solution. Muscles are stimulated at one end using bipolar electrodes and the propagated electrogram is recorded at the opposite end via a unipolar surface electrode. ERP is determined as above using the extrastimulus technique. Conduction time is obtained from a digital storage oscilloscope by measuring the interval between the stimulus artefact and the peak of the electrogram (i.e. the time required for the impulse to travel along the length of the muscle).

Atrial and vetricular ERP's are also measured in anaesthetised or conscious dogs by the extrastimulus technique whilst the atrium or right ventricle is being paced at a constant rate.

For human use the compounds of the formula (I) can be administered alone but will generally be administered in admixture with a pharmaceutical carrier selected with regard to the intended route of administration and standard pharmaceutical practice. They can be administered both to patients suffering from arrhythmias and also prophylactically to those likely to develop arrhythmias. For example they may be administered orally in the form of tablets containing such excipients as starch or lactose, or in capsules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other solutes, for example, enough salts or glucose to make the solution isotonic with blood.

For administration to man in the curative or prophylactic treatment of cardiac conditions such as ventricular and supraventricular arrhythmias, including atrial and ventricular fibrillation, it is expected that oral dosages of the compounds of the invention will be in the range of 1 to 75 mg daily, taken in up to 4 divided doses per day, for an average adult patient (70 kg). Thus for a typical adult patient, individual tablets or capsules might contain 1 to 25 mg of active compound, in a suitable pharmaceutically acceptable vehicle or carrier. Dosages for intravenous administration would be expected to be within the range 0.5 to 10 mg per single dose as required. A severe cardiac arrhythmia is preferably treated by the i.v. route in order to effect a rapid conversion to the normal rhythm. Variations on these dosages may occur depending on the weight and condition of the subject being treated as will be determined by the medical practitioner.

Thus the present invention provides a pharmaceutical composition comprising a compound of the formula (I) as defined above or pharmaceutically acceptable salt thereof, together with a pharmaceutically acceptable diluent or carrier.

The invention also provides a method of preventing or reducing cardiac arrhythmias in a human being, which comprises administering to said human an effective amount of a compound of formula (I) or pharmaceutically acceptable salt thereof, or of a pharmaceutical composition as defined above.

The invention yet further provides a compound of the formula (I) or pharmaceutically acceptable salt thereof, for use as an antiarrhythmic agent.

The invention also provides the use of a compound of the formula (I), or of a pharmaceutically acceptable salt thereof, for the manufacture of a medicament for the prevention or reduction of cardiac arrhythmias.

The following Examples, in which all temperatures are in °C., illustrate the invention:

EXAMPLE 1

N-{4-[1-(4-Pyridyl)piperidin-4-yl]phenyl}methanesulphonamide (i) 4-(4-Nitrophenyl)-1-(4-pyridyl)piperidine

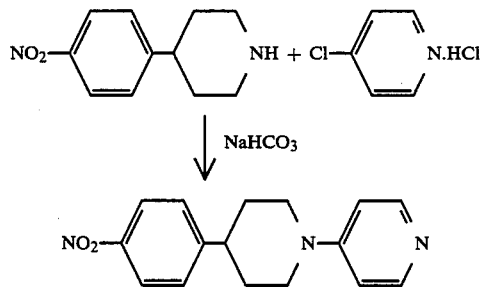

A mixture of 4-(4-nitrophenyl)piperidine [J. Chem. Soc. (B), 128, 1970] (4.12 g), 4-chloropyridine hydrochloride (3.00 g), sodium bicarbonate (5.04 g) and n-butanol (60 ml) was heated under reflux for 48 hours and then evaporated. The residue was partitioned between water and ethyl acetate. The organic phase was washed with water, dried ($Na_2SO_4$) and evaporated to give a solid which was chromatographed on silica gel. The column was eluted initially with ethyl acetate and then the eluent polarity was gradually increased to ethyl acetate/methanol (10:1). Earlier fractions contained impurity and the product was eluted in the later fractions. The product-containing fractions were combined and evaporated, and the residue was crystallised from ethyl acetate to give the title compound, (0.25 g), m.p. 173°–174°.

Analysis %: Found: C, 67.56; H, 5.97; N, 14.73; $C_{16}H_{17}N_3O_2$ requires: C, 67.82; H, 6.05; N, 14.83.

(ii) 4-(4-Aminophenyl)-1-(4-pyridyl)piperidine

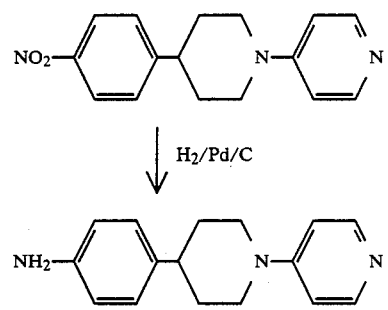

A mixture of the product from part (i) (0.24 g) and 5% palladium/carbon (25 mg) in methanol (20 ml) was hydrogenated at 3.5 bars and 21° for 3 hours. The catalyst was filtered off and the filtrate was evaporated to give the title compound, (0.21 g), m.p. 196°–197° (from ethyl acetate/hexane).

Analysis %: Found: C, 75.65; H, 7.34; N, 16.23; $C_{16}H_{19}N_3$ requires: C, 75.85; N, 7.56; N, 16.59.

(iii)
N-{4-[1-(4-Pyridyl)piperidin-4-yl]phenyl}methanesulphonamide

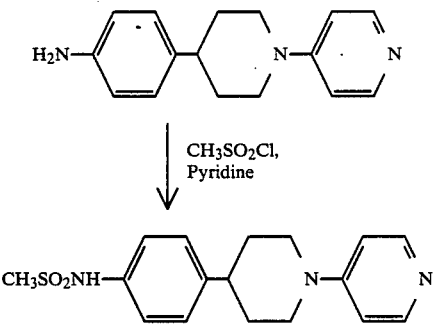

Methanesulphonyl chloride (0.076 g) was added dropwise to a stirred solution of the product from part (ii) above (0.152 g) in pyridine (5.0 ml) at 0°. The mixture was stirred at room temperature for 3 hours and then evaporated. The residue was dissolved in water and an excess of solid sodium bicarbonate was added. The solid was filtered off, washed with water, dried and crystallised from methanol/ethyl acetate to give the title compound, (0.065 g), m.p. 269°–271° (with decomp).

Analysis %: Found: C, 61.86; H, 6.41; N, 12.36; $C_{17}H_{21}N_3O_2S$ requires: C, 61.60; H, 6.39; N, 12.68.

EXAMPLE 2

4-[1-(4-Pyridyl)piperidin-4-yl]benzenesulfonamide (i) 4-(1-Acetylpiperidin-4-yl)benzenesulphonyl chloride

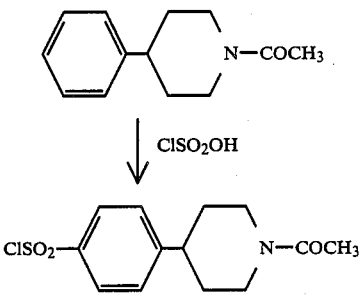

1-Acetyl-4-phenylpiperidine, [Chem. Abs., 75, 5728b (1971)] (16.30 g) was added portionwise over 1 hour to stirred chlorosulphonic acid (53.3 ml) at 0°. The solution was stirred at 0° for 1 hour, then at room temperature for 2 hours, and then finally poured cautiously onto an excess of ice. When the ice had melted the mixture was extracted several times with dichloromethane. The combined organic extracts were washed with water, dried ($Na_2SO_4$) and evaporated to give the title compound, (23.0 g), m.p. 133°-134°, used directly in the next step.

(ii) 4-(1-Acetylpiperidin-4-yl)benzenesulphonamide

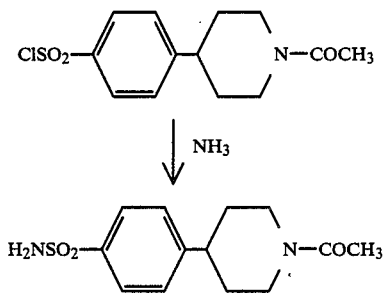

The product of (i) above (21.0 g) was added portionwise to a stirred mixture of concentrated aqueous ammonia solution (160 ml) and ethanol (160 ml). The mixture was warmed at 35° until solution was complete and then evaporated. The residue was triturated with water and the solid was filtered off and dried to give the title compound, (18.0 g), m.p. 196°-197° (from ethanol).

Analysis %: Found: C, 55.59; H, 6.56; N, 9.86; $C_{13}H_{18}N_2O_3S$ requires: C, 55.29; H, 6.42; N, 9.92.

(iii) 4-(4-Piperidinyl)benzenesulphonamide

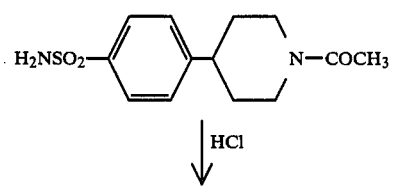

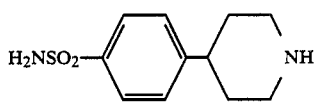

A mixture of the product of part (ii) above (17.0 g) and 5N aqueous hydrochloric acid (150 ml) was heated under reflux for 3 hours. The resulting solution was evaporated and the residue was dissolved in the minimum volume of water. The solution was made basic (to a pH of about 8-9) by the addition of solid sodium bicarbonate. The solid was filtered off, washed with a little water and crystallised from ethanol/methanol (2:1) to give the title compound, (7.70 g), m.p. 229°-230°.

Analysis %: Found: C, 55.21; H, 6.93; N, 11.59; $C_{11}H_{16}N_2O_2S$ requires: C, 54.97; H, 6.71; N, 11.66.

(iv) 4-[1-(4-Pyridyl)piperidin-4-yl]benzenesulphonamide

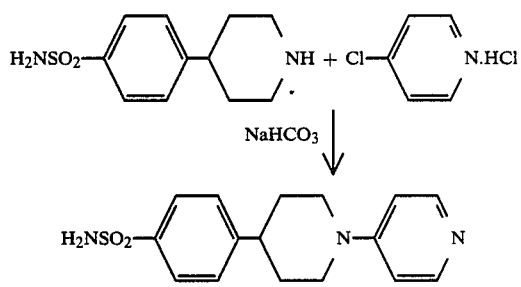

A mixture of the product of part (iii) above (3.75 g), 4-chloropyridine hydrochloride (2.34 g), sodium bicarbonate (3.93 g) and isoamyl alcohol (60 ml) was heated under reflux for 30 hours and then evaporated. The residue was triturated with water and the mixture was filtered. The solid was washed well with water and crystallised from methanol/water to give the title compound (0.43 g), m.p. 295° (with decomp).

Analysis %: Found: C, 60.60; H, 5.84; N, 13.10; $C_{16}H_{19}N_3O_2S$ requires: C, 60.54; H, 6.03; N, 13.24.

EXAMPLE 3

N-Methyl-4-[1-(4-pyridyl)piperidin-4-yl]benzenesulphonamide (i) N-Methyl-4-(1-acetylpiperidin-4-yl)benzenesulphonamide

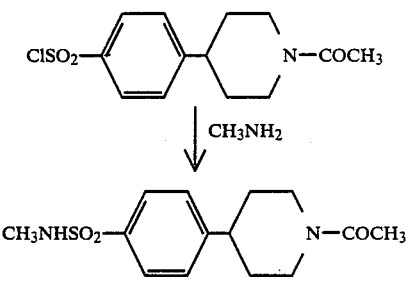

Reaction of 4-(1-acetylpiperidin-4-yl)benzenesulphonyl chloride (16.0 g) [the product of Example 2(i)] with an excess of aqueous methylamine (100 ml, 30%) in ethanol (10 ml) according to the method of Example 2(ii) gave the title compound, (15.0 g), used directly in the next stage.

(ii) N-Methyl-4-(4-piperidinyl)benzenensulphonamide

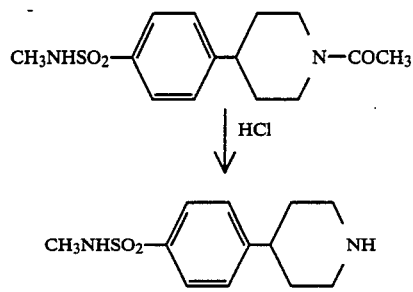

Hydrolysis of the product of part (i) above (15.0 g) according to the method of Example 2(iii) using 5N hydrochloric acid (100 ml) gave the title compound, (7.9 g), m.p. 170°–172°.

Analysis %: Found: C, 56.19; H, 7.14; N, 10.23; $C_{12}H_{18}N_2O_2S$ requires: C, 56.66; H, 7.13; N, 11.02.

(iii)
N-Methyl-4-[1-(4-pyridyl)piperidin-4-yl]benzenesulphonamide

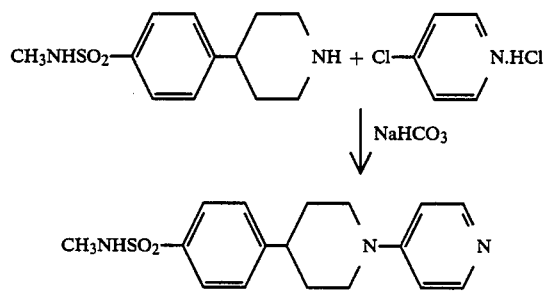

A mixture of the product of part (ii) above (0.50 g), 4-chloropyridine hydrochloride (0.60 g), sodium bicarbonate (0.50 g) and n-butanol was heated under reflux for 30 hours and then evaporated. The residue was partitioned between dichloromethane and water. The aqueous layer was extracted several times with dichloromethane. The organic layers were combined, washed with water, dried (MgSO4) and evaporated. The residue was chromatographed on silica gel. Elution with dichloromethane, gradually increasing the polarity to dichloromethane/methnol (19:1), first gave some impurity followed by the desired product. The product-containing fractions were evaporated and the residue was crystallised from ethanol/ethyl acetate to give the title compound, (35 mg), m.p. 225°–228°.

Analysis %: Found: C, 61.42; H, 6.47; N, 12.59; $C_{17}H_{21}N_3O_2S$ requires: C, 61.60; H, 6.39; N, 12.68.

EXAMPLE 4

4-[1-(4-Aminopyrid-2-yl)piperidin-4-yl]benzenesulphonamide (i)
4-[1-(4-Nitropyrid-2-yl)piperidin-4-yl]benzenesulphonamide

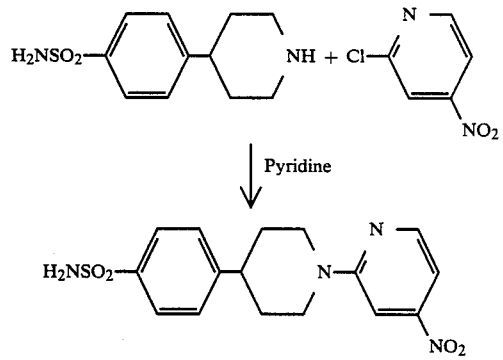

A solution of 4-(4-piperidinyl)benzensulphonamide [the product of Example 2(iii)] (0.46 g) and 2-chloro-4-nitropyridine (0.30 g) in pyridine (10 ml) was heated under reflux for 5 hours and then evaporated. The residue was partitioned between dichloromethane and 10% aqueous sodium carbonate solution. The aqueous layer was extracted several times with dichloromethane nd the combined organic extracts were dried (MgSO4) and evaporated. The residue was chromatographed on silica gel. Elution with dichloromethane/methanol (99:1) first gave impurity followed by the pure product. The product-containing fractions were combined and evaporated to give the title compound, (0.15 g), m.p. 215°–217°.

Analysis %: Found: C, 52.75; H, 4.89; N, 15.55; $C_{16}H_{18}N_4O_4S$ requires: C, 53.02; H, 5.00; N, 15.46.

(ii)
4-[1-(4-Aminopyrid-2-yl)piperidin-4-yl]benzenesulphonamide

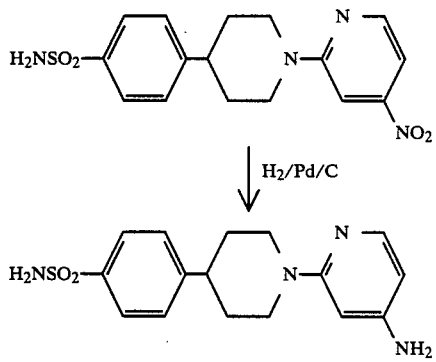

A mixture of the product from part (i) (100 mg) and 5% palladium/carbon (25 mg) in ethanol (25 ml) and acetic acid (25 ml) was hydrogenated at 3.5 bars at room temperature for 3 hours. The catalyst was filtered off, the filtrate was evaporated and the residue was chromatographed on silica gel. Elution with dichloromethane/ethanol (19:1) gave some impurity and further elution with dichloromethane/ethanol/concentrated aqueous ammonia (90:10:1) gave the pure product. The combined product-containing fractions were evaporated to give the title compound as a monohydrate, m.p. 290°–295° (with decomp).

Analysis %: Found: C, 54.86; H, 6.62; N, 15.85; $C_{16}H_{20}N_4O_2S \cdot H_2O$ requires: C, 54.85; H, 6.32; N, 15.99.

EXAMPLE 5

N-{4-[1-(1-Methylimidazol-2-yl)piperidin-4-yl]phenyl}methanesulphonamide (i)
N-Methyl-4-(4-nitrophenyl)piperidin-1-ylcarbothioamide

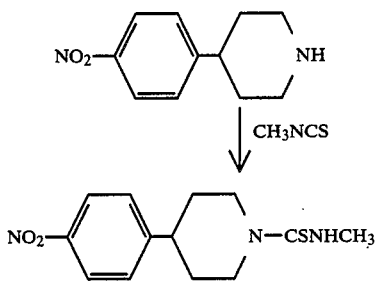

A solution of methyl isothiocyanate (2.60 g) in dichloromethane (15 ml) was added dropwise to a stirred solution of 4-(4-nitrophenyl)piperidine (7.20 g) in dichloromethane (60 ml). The solution was stirred for 3 hours at room temperature and then allowed to stand for 18 hours. It was evaporated and the residue was chromatographed on silica gel. Elution with ethyl acetate followed by ethyl acetate/methanol (20:1) first gave impurity followed by the pure product. The combined product-containing fractions were evaporated and the solid was crystallised from ethyl acetate to give the title compound (4.50 g), m.p. 143°–144°.

Analysis %: Found: C, 56.10; N, 6.34; N, 14.88; $C_{13}H_{17}N_3O_2S$ requires: C, 55.89; H, 6.14; N, 15.04.

(ii)
N-Methyl-4-(4-nitrophenyl)piperidin-1-ylcarboximidothioic acid methyl ester hydroiodide

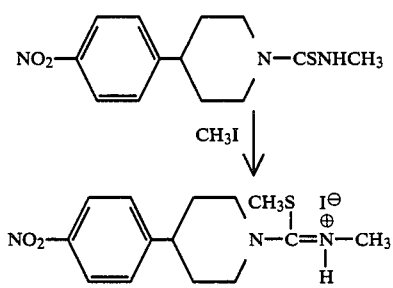

A solution of iodomethane (2.55 g) in methanol (5 ml) was added dropwise over 10 minutes to a solution of the product from part (i) (4.20 g) in methanol (50 ml). The solution was heated under reflux for 2 hours and then evaporated to give the title compound, (6.30 g), m.p. 106°–107° (from methanol/ethyl acetate).

Analysis %: Found: C, 39.65; H, 4.81; N, 9.64; $C_{14}H_{19}N_3O_2S \cdot HI$ requires: C, 39.91; H, 4.79; N, 9.97.

(iii)
1-(1-Methylimidazol-2-yl)-4-(4-nitrophenyl)piperidine

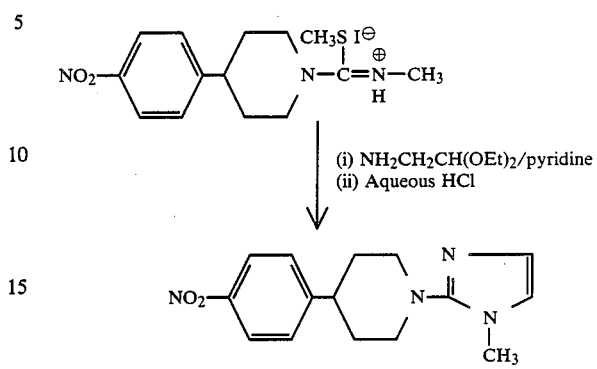

Aminoacetaldehyde diethyl acetal (0.88 g) was added dropwise over 5 minutes to a stirred solution of the product from part (ii) (2.53 g) in pyridine (15 ml) at room temperature. The solution was heated under reflux with stirring for 6 hours and then evaporated to dryness. The residue was dissolved in 2N hydrochloric acid (36 ml) and the solution was heated under reflux for 1.5 hours and evaporated. The residue was dissolved in water and the solution was basified to pH 8–9 by the addition of saturated aqueous sodium bicarbonate solution. The mixture was extracted several times with ethyl acetate and the combined organic extracts were washed with water and dried ($Na_2SO_4$). Evaporation of the solvent gave a solid which was chromatographed on silica gel. Elution with ethyl acetate, gradually increasing the polarity of the eluent to ethyl acetate/methanol (5:1), gave a solid which was crystallised from ethyl acetate to give the title compound, (0.60 g), m.p. 155°–156°.

Analysis %: Found: C, 62.86; H, 6.10; N, 19.44; $C_{15}H_{18}N_4O_2$ requires: C, 62.92; H, 6.34; N, 19.57.

(iv)
4-(4-Aminophenyl)-1-(1-methylimidazol-2-yl)piperidine

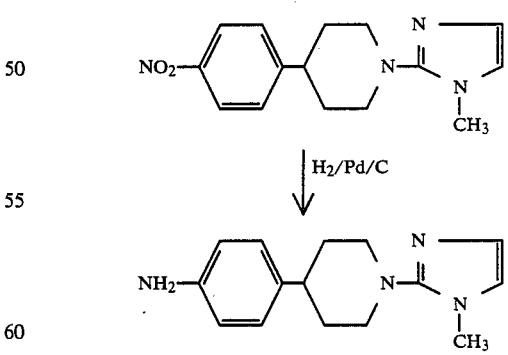

Hydrogenation of the product from part (iii) above (0.50 g) in methanol (30 ml) according to the method of Example 1(ii) gave the title compound, (0.43 g), m.p. 187°–188° from ethyl acetate/hexane.

Analysis %: Found: C, 70.40; H, 7.91; N, 21.80; $C_{15}H_{20}N_4$ requires: C, 70.28; H, 7.86; N, 21.86.

(v)
N-{4-[1-(1-Methylimidazol-2-yl)piperidin-4-yl]phenyl}methanesulphonamide

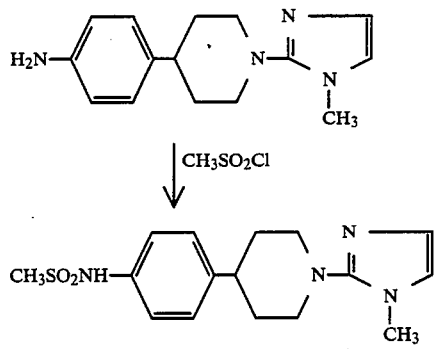

Treatment of the product from part (iv) above (0.31 g) with methanesulphonyl chloride (0.15 g) in pyridine (10 ml) by the method of Example 1(iii) gave the title compound, (0.29 g), m.p. 201°–202°.

Analysis %: Found: C, 57.14; H, 6.60; N, 16.56; $C_{17}H_{24}N_4O_2S$ requires: C, 57.46; H, 6.63; N, 16.75.

EXAMPLE 6

N-{4-[1-(1,5-Dimethylimidazol-2-yl)piperidin-4-yl]phenyl}methanesulphonamide (i)
1-(1,5-Dimethylimidazol-2-yl)-4-(4-nitrophenyl)piperidine

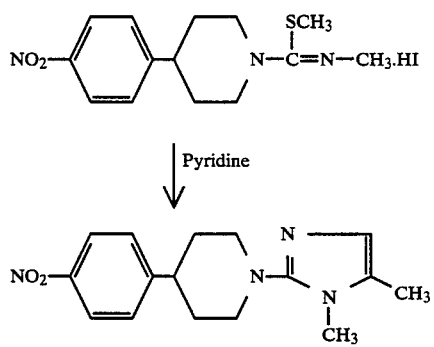

Propargylamine (1.93 g) was added dropwise over 2 minutes to a stirred solution of N-methyl-4-(4-nitrophenyl)piperidin-1-ylcarboximidothioic acid methyl ester hydroiodide [the product of Example 5(ii)] (2.95 g) in pyridine (20 ml) at room temperature and the solution was heated under reflux for 2 hours and then evaporated to dryness. Water was added to the residue and the mixture was basified to pH 8–9 with saturated aqueous sodium bicarbonate solution. The mixture was extracted several times with ethyl acetate, and the combined extracts were washed with water and dried ($Na_2SO_4$). Evaporation of the solvent gave a solid which was chromatographed on silica gel. Elution with ethyl acetate/methanol (5:1) first gave impurity followed by the pure product. The product-containing fractions were combined and evaporated and the residue was crystallised from methanol/ethyl acetate to give the title compound, (0.93 g), m.p. 178°–179°.

Analysis %: Found: C, 64.36; H, 6.80; H, 18.72; $C_{16}H_{20}N_4O_2$ requires: C, 63.98; H, 6.71; N, 18.65.

(ii)
4-(4-Aminophenyl)-1-(1,5-dimethylimidazol-2-yl)piperidine

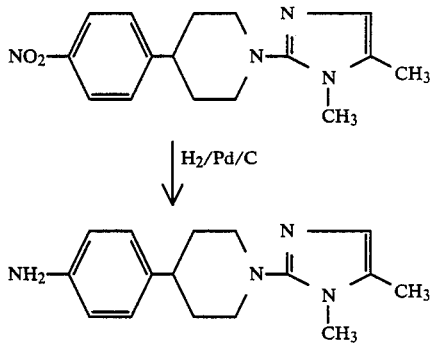

Hydrogenation of the product from part (i) above (0.60 g) in methanol (50 ml) according to the method of Example 1(ii) gave the title compound, (0.53 g), m.p. 219°–220° (with decomp).

Analysis %: Found: C, 70.69; H, 8.26; N, 21.10; $C_{16}H_{22}N_4$ requires: C, 71.07; H, 8.20; N, 20.73.

(iii)
N-{4-[1-(1,5-Dimethylimidazol-2-yl)piperidin-4-yl]phenyl}methanesulphonamide

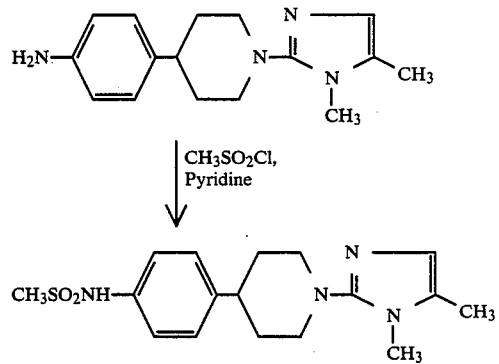

Treatment of the product from part (ii) above (0.46 g) with methanesulphonyl chloride (0.22 g) in pyridine (12 ml) according to the method fo Example 1(iii) gave the title compound, (0.40 g), m.p. 225°–226°.

Analysis %: Found: C, 58.29; H, 7.02; N, 15.94; $C_{17}H_{24}N_4O_2S$ requires: C, 58.59; H, 6.94; N, 16.08.

EXAMPLE 7

4-[1-(1,5-Dimethylimidazol-2-yl)piperidin-4-yl]benzenesulphonamide (i)

N-Methyl-4-(4-sulphamoylphenyl)piperidin-1-ylcarbothioamide

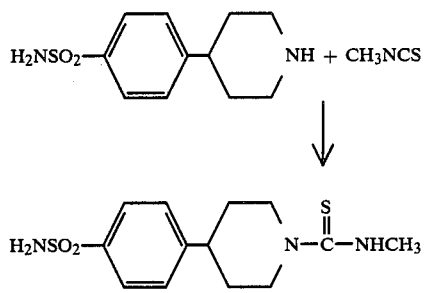

A solution of methyl isothiocyanate (0.73 g) in methanol (10 ml) was added dropwise to a stirred solution of 4-(4-piperidinyl)benzenesulphonamide [the product of Example 2(iii)] (2.40 g) in methanol (90 ml) and the solution was stirred for 3 hours at room temperature and then allowed to stand for 18 hours. It was then evaporated to about ⅓ volume, filtered and allowed to stand until crystallisation was complete. The solid was filtered off and dried to give the title compound, (2.55 g), m.p. 208°–209°.

Analysis %: Found: C, 49.75; H, 6.13; N, 13.49; $C_{13}H_{19}N_3O_2S_2$ requires: C, 49.81; H, 6.11; N, 13.41.

(ii)

N-Methyl-4-(4-sulphamoylphenyl)piperidin-1-ylcarboximidothioic acid methyl ester hydroiodide

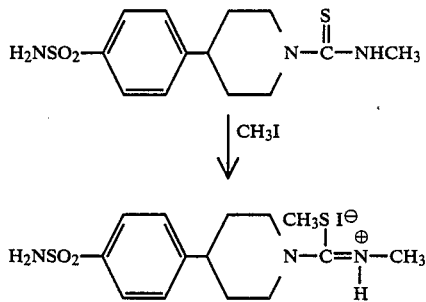

Iodomethane (1.4 g) was added dropwise to a solution of the product of part (i) above (2.38 g) in methanol (110 ml) and the solution was stirred for 1 hour at room temperature. A further portion of iodomethane (1.14 g) was added and the solution was stirred for 20 hours at room temperature and then evaporated. The residue was triturated with ethyl acetate containing a trace of methanol to give a solid which was filtered off and dried to give the title compound, (3.40 g), m.p. 201°–202° (from methanol/ethyl acetate).

Analysis %: Found: C, 37.16; H, 4.92; N, 9.30; $C_{14}H_{21}N_3O_2S_2.HI$ requires: C, 36.92; H, 4.87; N, 9.23.

(iii)

4-[1-(1,5-Dimethylimidazol-2-yl)piperidin-4-yl]benzenesulphonamide

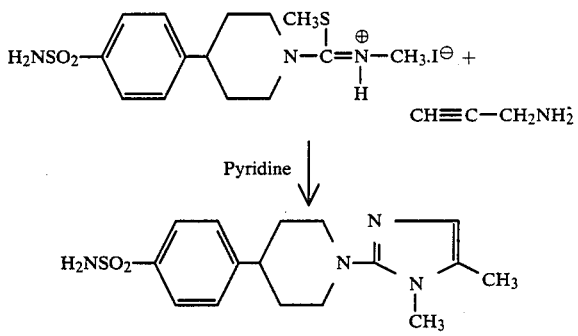

Propargylamine (1.10 g) was added dropwise to a stirred solution of the product from part (ii) above (1.82 g) in pyridine (12 ml) and the solution was heated under reflux with stirring for 5 hours and then evaporated. Water was added to the residue and the mixture was basified to a pH 8–9 with saturated aqueous sodium bicarbonate solution. The solid was filtered off, washed with water and crystallised from isopropanol/water to give the title compound, (0.63 g), m.p. 256°–257° (with decomp.) which was shown by n.m.r. spectroscopy to contain 0.25 mole of isopropanol.

Analysis %: Found: C, 57.69; H, 6.71; N, 15.80; $C_{16}H_{22}N_4O_2S$, 0.25 $C_3H_7OH$ requires: C, 57.56; H, 6.92; N, 16.00.

We claim:

1. A compound of the formula:

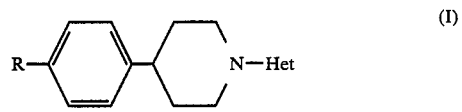

or a pharmaceutically acceptable salt thereof; wherein R is $R^3SO_2NH-$, $R^3CONH-$ or $R^1R^2NSO_2-$;

$R^1$ and $R^2$ are each independently H or $C_1-C_4$ alkyl; $R^3$ is $C_1-C_4$ alkyl, $C_3-C_7$ cycloalkyl or $-NR^1R^2$ where $R^1$ and $R^2$ are as defined above; and Het is either (a) a 2-, 3- or 4-pyridyl group unsubstituted or substituted by a $C_1-C_4$ alkyl or an amino group, or (b) a 2-imidazolyl group unsubstituted or substituted by one or two $C_1-C_4$ alkyl groups, said two $C_1-C_4$ alkyl groups being the same or different.

2. A compound as claimed in claim 1, wherein R is $CH_3SO_2NH-$, $CH_3NHSO_2-$ or $H_2NSO_2-$.

3. A compound as claimed in claim 1, wherein Het is 4-pyridyl, 4-amino-2-pyridyl, 1-methyl-2-imidazolyl or 1,5-dimethyl-2-imidazolyl.

4. A compound as claimed in claim 2, wherein Het is 4-pyridyl, 4-amino-2-pyridyl, 1-methyl-2-imidazolyl or 1,5-dimethyl-2-imidazolyl.

5. A compound as claimed in claim 3 wherein Het is 4-pyridyl and R is $CH_3SO_2NH-$ or $H_2NSO_2-$.

6. A compound as claimed in claim 4, wherein Het is 4-pyridyl and R is $CH_3SO_2NH-$ or $H_2NSO_2-$.

7. A pharmaceutical composition for treating cardiac arrhythmia comprising an antiarrhythmic effective amount of a compound of claim 1 and a pharmaceutically acceptable diluent or carrier.

8. A method of treating cardiac arrhythmia in mammals comprising administering to a mammal in need of such treatment on antiarrhythmic effective amount of a compound of claim 1.

9. A method according to claim 8, wherein said mammal is a human.

10. A compound of the formula:

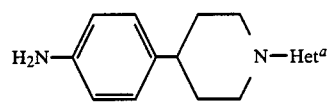

(IX)

where Het$^a$ is either (a) a 2-, 3- or 4-pyridyl group unsubstituted or substituted by a $C_1$-$C_4$ alkyl, or (b) a 2-imidazolyl group unsubstituted or substituted by one or two $C_1$-$C_4$ alkyl groups, said two $C_1$-$C_4$ alkyl groups being the same or different.

* * * * *